(12) United States Patent
Dmuschewsky

(10) Patent No.: US 10,166,029 B2
(45) Date of Patent: Jan. 1, 2019

(54) JIG FOR DETERMINING A PATIENT-ADAPTED IMPLANT SIZE OF THE FEMORAL IMPLANT OF A KNEE ENDOPROSTHESIS

(71) Applicant: Waldemar Link GmbH & Co. KG, Hamburg (DE)

(72) Inventor: Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 15/540,853

(22) PCT Filed: Sep. 24, 2015

(86) PCT No.: PCT/EP2015/071982
§ 371 (c)(1),
(2) Date: Jun. 29, 2017

(87) PCT Pub. No.: WO2016/110338
PCT Pub. Date: Jul. 14, 2016

(65) Prior Publication Data
US 2017/0348009 A1    Dec. 7, 2017

(30) Foreign Application Priority Data
Jan. 6, 2015  (DE) ................ 10 2015 100 049

(51) Int. Cl.
*A61B 17/15*    (2006.01)
*A61F 2/46*    (2006.01)
(Continued)

(52) U.S. Cl.
CPC .......... *A61B 17/155* (2013.01); *A61F 2/4657* (2013.01); *A61B 2090/0807* (2016.02);
(Continued)

(58) Field of Classification Search
CPC ........................ A61B 17/155; A61B 17/154
See application file for complete search history.

(56) References Cited

U.S. PATENT DOCUMENTS 5,624,444 A    4/1997    Wixon et al.
5,810,831 A    9/1998    D'antonio
(Continued)

FOREIGN PATENT DOCUMENTS

DE    602004011420 T2    1/2009
EP    2277460 A1    1/2011
(Continued)

*Primary Examiner* — Christian Sevilla
(74) *Attorney, Agent, or Firm* — Sand & Sebolt

(57) ABSTRACT

A jig for determining a patient-adapted implant size of a femoral implant of a knee endoprosthesis. The jig has a main body, a probe part movable relative to the main body along a measuring direction. The probe part has an arm with a tip placeable on an anterior reference point of the femur's distal end, two contact pieces for placing on and referencing the medial and lateral posterior condyle of the femur's distal end, and at least one scale and pointer for indicating the probe part's position in the measuring direction relative to the contact pieces. The distance of the probe tip from the contact pieces is adjustable such that the distance is different with respect to the two contact pieces and, for each contact piece, a dedicated scale and an associated pointer are provided for the indication of the probe part's position relative to the respective contact piece.

10 Claims, 7 Drawing Sheets

(51) Int. Cl.
 *A61B 90/00* (2016.01)
 *A61F 2/38* (2006.01)
 *A61F 2/30* (2006.01)

(52) U.S. Cl.
 CPC ..... *A61B 2090/0813* (2016.02); *A61F 2/3859* (2013.01); *A61F 2002/30471* (2013.01); *A61F 2002/30617* (2013.01); *A61F 2002/4658* (2013.01); *A61F 2002/4668* (2013.01)

(56) References Cited

U.S. PATENT DOCUMENTS

| | | |
|---|---|---|
| 2004/0220583 A1 | 11/2004 | Pieczynski et al. |
| 2005/0209600 A1 | 9/2005 | Fencl et al. |
| 2009/0143783 A1 | 6/2009 | Dower |
| 2014/0025081 A1 | 1/2014 | Lorio et al. |

FOREIGN PATENT DOCUMENTS

| | | |
|---|---|---|
| WO | 94/000056 A1 | 1/1994 |
| WO | 2005/046432 A2 | 5/2005 |

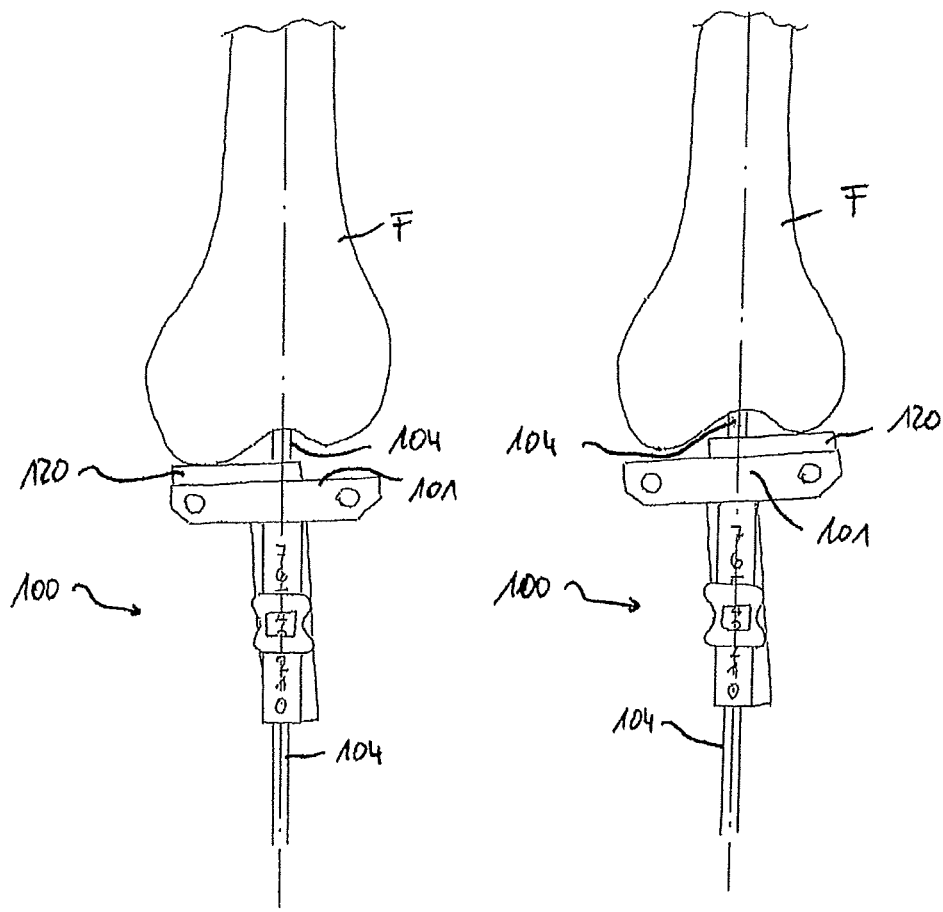

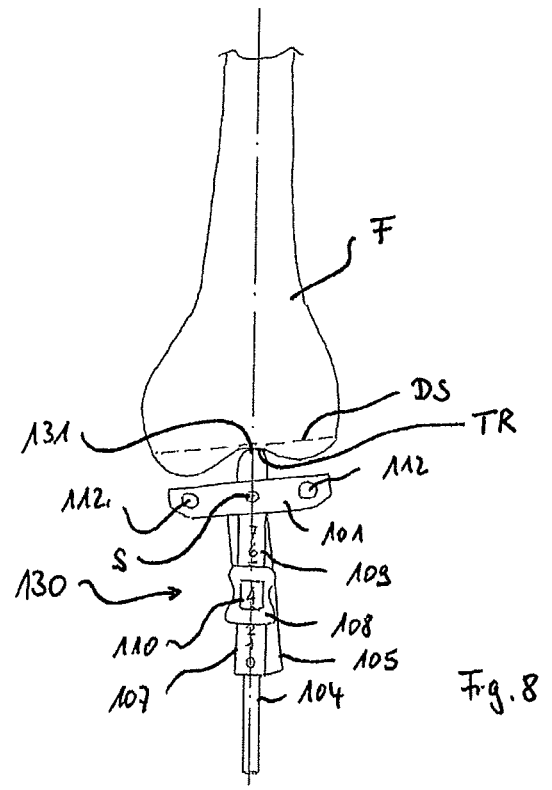
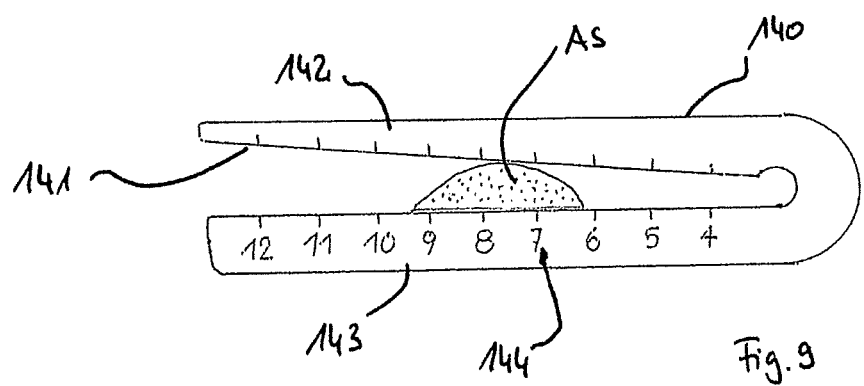

JIG FOR DETERMINING A PATIENT-ADAPTED IMPLANT SIZE OF THE FEMORAL IMPLANT OF A KNEE ENDOPROSTHESIS

TECHNICAL FIELD

The present invention relates to a jig for determining a patient-adapted implant size of the femoral implant of a knee endoprosthesis that has a main body, a probe part displaceable relative to the main body along a measuring direction, wherein the probe part has a probe arm with a probe tip for contacting on an anterior reference point (RP) of the distal end of the patient's femur, two contact pieces for contacting on and referencing on respectively the medial and the lateral posterior condyle of the distal end of the patient's femur and at least one scale and an associated indicator for indicating a location of the probe part in the measuring direction relative to at least one of the contact pieces for the specification of a suitable implant size. This jig is to be used in particular in conjunction with primary care, in other words, the initial replacement of the worn natural knee joint with a prosthesis.

BACKGROUND

A well-known solution in the case of knee joints which have been damaged by wear or by other conditions such as, for example, tumors, and which no longer allow the patient concerned to move in a normal and, in particular, pain-free manner, is to replace the joint surfaces of the bones concerned, in other words, on the distal end of the femur and on the dorsal tibia side, with suitable implants. For this purpose, various renowned commercial suppliers provide suitable implants or implant families, which are now routinely inserted into affected patients.

Different implant sizes must be used due to differing anatomical proportions in the patients concerned. For example, patients have differently sized bone sections or bone ends at the distal femur, but also at the dorsal tibia. For this purpose, the suppliers offer, usually in the respective implant series, suitable implants (femoral implants for replacement of the distal femoral joint surfaces, tibial implants for replacement of the dorsal tibia joint surfaces) in different sizes. Sets with between 5 and 10 different implant sizes are common.

Although preoperative diagnostics, in particular using X-ray images or CT scans, provides the attending physician and surgeon with initial indications not only regarding the finding of wear or of pathological damage of the knee joint, but also regarding the proportions of the natural joint mechanism, it is nevertheless not possible to undertake precise sizing of the respective implant (femoral implant, tibial implant) to be used solely on the basis of the preoperative diagnostics, and the surgeon still has to make an appropriate choice during the operation. The surgeon additionally often obtains a definitive diagnostic picture only during the operation and, in addition to determining the selectable size of the respective implant part, in particular of the femoral implant, he also determines the precise alignment for the attachment of this implant part to the remaining bone (in particular to the section of the distal femur remaining after the required resection cutting). In many cases, an arrangement of the implant aligned along the axis extending from medial to lateral on the plateau formed by the distal femur cut is not selected, instead, an alignment which is inclined relative to this axis by an external implant angle is set, said inclination typically being able to be in a range between approx. 0 and 7°, typically inclined from medial to lateral.

In a typical procedure for carrying out the preparatory resections for the femoral implant which is to be selected with respect to the suitable size, the distal condyle cut is firstly realized once the patient's knee joint has been exposed with the knee in a bent position, in other words, in flexion (the bent position typically being approximately 90°), in which procedure a first planar cut surface is created at the point at which the distal condyles, in other words joint surfaces, of the femur are arranged. Subsequently, the determination of the implant size which is suitable for the patient is undertaken typically using a jig by means of measurement of the anatomical dimensions from anterior to posterior. The jig has a main body, a probe part displaceable relative to the main body along a measuring direction, wherein the probe part has a probe arm with a probe tip for contacting on an anterior reference point (RP) of the distal end of the patient's femur, two contact pieces for contacting on and referencing on respectively the medial and the lateral posterior condyle of the distal end of the patient's femur and at least one scale and an associated indicator for indicating a location of the probe part in the measuring direction relative to at least one of the contact pieces for the specification of a suitable implant size. For this purpose, the jig with the contact pieces is placed under the posterior condyles, which lie on the tibial plateau in the flexion position, and by means of the probe arm, or more specifically by means of its probe tip, an anterior reference point on the femur is contacted which the surgeon considers to be suitable, typically the uppermost anterior point which is situated dorsal relative to the anterior condyle end portions. The probe part is correspondingly displaced in the measuring direction, and it is then possible to read an implant size which is suitable for the patient from the scale by means of the location of the indicator relative to this scale.

Examples of such jigs are described together with the corresponding procedure for their use for example in WO 94/00056 A1, WO 2005/046432 A2, U.S. Pat. Nos. 5,624,444, 5,810,831, US 2004/0220583 A1 and US 2009/0143783 A1.

In addition, jigs of the type that have a main body, a probe part displaceable relative to the main body along a measuring direction, wherein the probe part has a probe arm with a probe tip for contacting on an anterior reference point (RP) of the distal end of the patient's femur, two contact pieces for contacting on and referencing on respectively the medial and the lateral posterior condyle of the distal end of the patient's femur and at least one scale and an associated indicator for indicating a location of the probe part in the measuring direction relative to at least one of the contact pieces for the specification of a suitable implant size are known, in which devices for the specification of an external rotation angle of the implant are additionally provided on the main body, said devices having pinholes through which, after setting of the desired rotation, corresponding pins can be driven into the first contact surface of the implant created by the distal condyle cut, for the purpose of further orientation and alignment of the implant in its angular position relative to a line extending from medial to lateral by means of the orientation of the cutting jig, correspondingly carried out with the help of these pins, for the additional resection cuts to be realized for the shaping of the femur. One example of such a jig is described in DE 60 2004 011 420 T2, another example is the jig presented by the US supplier Zimmer. Inc. in their brochure "Zimmer® NexGen® CR-Flex and LPS- Flex Knees Surgical Technique with Posterior Referencing Instrumentation", which comprises on the main body, in addition to the probe part, another rotating body which can be pivoted about a pivot pin, by means of which the corresponding external angular setting can be specified and in which the above-mentioned pinholes are formed.

A common factor in all of the above-mentioned known jigs for determining the patient-adapted implant size of the femoral implant of a knee endoprosthesis is that the contact pieces for the contacting on and for the referencing on the medial and the lateral posterior condyle respectively are firmly connected to the main body so that, relative thereto, only the probe part can be moved in the measuring direction for the determination of the size.

However, in particular when specification of an external angular setting is to be realized together with the determination of size, this design can lead to measuring errors and consequently to problems when selecting the suitable implant size.

SUMMARY

The problem addressed by the present invention is to remedy this issue and to solve the problems associated with it.

This problem is solved by means of a jig for determining a patient-adapted implant size of the femoral implant of a knee endoprosthesis wherein, in the jig, the contact pieces can be moved relative to the main body in such a way that a distance of the probe tip to the contact pieces which is projected on the measuring direction can be set for the contact pieces in such a way that this distance is different with respect to the two contact pieces, and in that each contact piece is provided with its own scale and an associated indicator for indicating a location of the probe part in the measuring direction relative to the respective contact piece and for the resulting specification of a suitable implant size. Advantageous further developments of a jig according to the invention includes that the jig has a coupling existing between the contact pieces, which, in the case of a relative movement of the one contact piece relative to the main body, also produces a relative movement of the other contact piece relative to the main body. Furthermore, the jig is characterized by a basic position, in which the two contact pieces have the same distance to the probe tip projected on the measuring direction, wherein the coupling ensures by means of each relative movement out of the basic position between a first of the contact pieces and the main body that there is a relative movement of the second of the contact pieces and the main body, which leads to a setting of the contact pieces in such a way that they have different distances to the probe tip projected on the measuring direction. The contact pieces each have an extension which extends in the measuring direction and which is firmly connected to the contact piece, with the extensions being connected to one another by means of two cross pieces extending parallel to one another, the cross pieces being connected in an articulated manner at one connection point to the respective extension, so that the two extensions and the two cross pieces form a parallelogram four point joint. The cross pieces are connected in an articulated manner to the main body in such a way that these cross pieces can be pivoted in a coupled manner relative to the main body. Each cross piece is connected in an articulated manner to the main body at an attachment point situated centrally between the two connection points, at which it is connected in an articulated manner to one of the two extensions. Furthermore, the jig may be characterized by at least one angle scale and an angle indicator which cooperates with said angle scale for indicating a pivot angle about which the cross pieces are pivoted relative to a starting position. The starting position may be the basic position. The jig may further be characterized by a handle which is connected to the main body and by a locking means for locking parts of the jig which can be moved relative to each other.

BRIEF DESCRIPTION OF THE DRAWINGS

FIG. 7a shows a first depiction of the alignment instrument of FIG. 6 in application for alignment in a targeted manner on the medial or the lateral condyle;

FIG. 7b shows a second depiction of the alignment instrument of FIG. 6 in application for alignment in a targeted manner on the medial or the lateral condyle;

FIG. 8 shows, in a depiction comparable with the depictions in FIGS. 7a and 7b, an alternative alignment instrument for the distal femur cut in application and FIG. 9 shows a gauge for a size determination of the section of a condyle for assisting with the implant size determination.

Additional advantages and features of the invention shall emerge from the description below on the basis of an exemplary embodiment with reference to the corresponding figures attached to this application.

DETAILED DESCRIPTION OF THE PRESENT INVENTION

Figure 1:
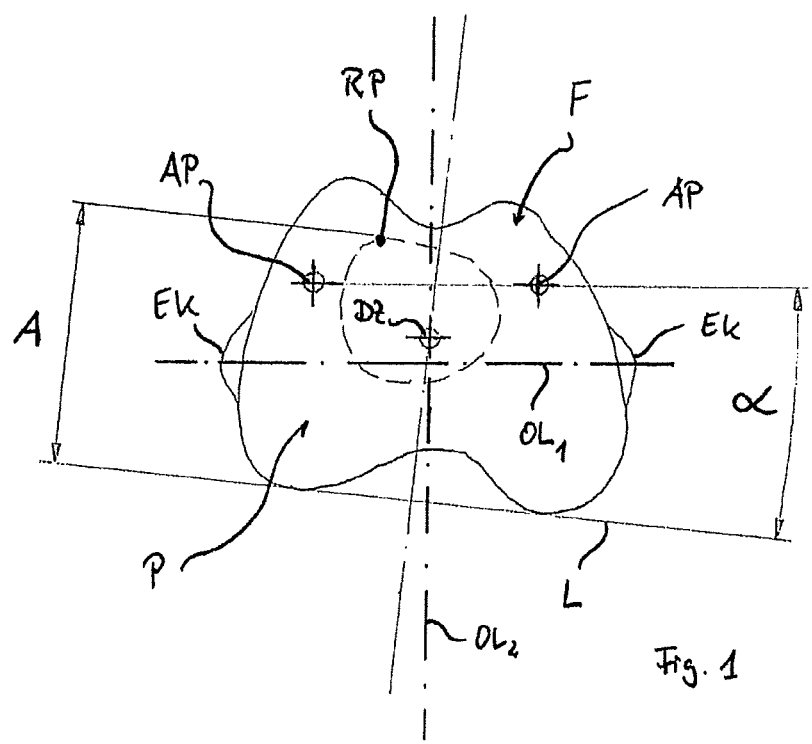
FIG. 1 shows a schematic depiction intended to clarify the problem of the measuring error which is encountered in the known jigs according to the prior art.

As FIG. 1 shows, the tilting relative to the fixed measuring architecture results in aberration of the actual distances in the tilted measuring direction, specifically varying with respect to medial or lateral. FIG. 1 depicts a schematic view of the distal end of a femur F, said distal end already having been prepared by means of a distal cut forming a plane surface P.

It is firstly possible to observe two orientation lines OL1 and OL2 which are determined by the anatomy and which are usually used by the operating surgeons as orientation aids. The first of these lines, the orientation line OL1 extends between the lateral extremes of the epicondyles EK, and the second orientation line OL2 connects the lower surfaces situated between the lateral and the medial condyle at approximately their lowest points.

It is also possible to observe a reference point RP which, displaced proximally from the distal end of the femur F, lies beyond the condyles on the femoral shaft, and which a surgeon contacts on by means of the probe of the conventional jig. The second reference for size determination is formed by the connecting line of the posterior condyles, depicted here as line L. This provides a distance A to the reference point RP determined perpendicular to this line L, which distance determines the sizing of the femoral implant. The figure now shows that, after the size determination as described above, a definition of the implant angle is undertaken, by realizing a rotation about the angle or obtaining the angular offset $\alpha$ around a rotation center DZ. The rotation for the purpose of alignment takes place relative to the line L, so that the alignment points AP are obtained on a line tilted correspondingly by this angle $\alpha$ relative to the line L, which alignment points are subsequently used for the continuation of the cuts corresponding to the attachment of the femoral implant which is to be provided tilted by the implant angle.

However, as can be easily observed here, the medial or lateral alignment points now no longer have a uniform distance to the referenced posterior condyles, but rather, the alignment point AP depicted on the left in FIG. 1 has a smaller distance to the respective posterior reference condyle and the alignment point AP depicted on the right in the figure has a lesser distance to the respective posterior reference condyle.

That is to say that, in the procedure sketched out in FIG. 1 and which is currently standard, before a tilting occurs, a certain implant size is determined in the measurement from posterior to anterior which is defined as suitable for the patient, and after the tilting corresponding errors are produced, which are not detected and thus are also not corrected. In practice it has been found that the previously determined implant size is often not appropriate in this respect, so that either the implant has to be replaced and another size has to be used, which involves a second resection for the purpose of adapting the corresponding cuts, or alternatively, in application of his experience an experienced surgeon directly selects an implant size diverging from the determined size, which implant size is then suitable after the tilting.

Only one of the two posterior condyles, e.g. medial, is therefore actually made reference to here, in particular due to the lateral arrangement of the anterior reference point, and the size is determined on the basis of this reference, without however also considering the parameters on the second side, in other words, in the example above, with regards to the lateral posterior condyle.

According to the invention, a jig for determining a patient-adapted implant size of the femoral implant of a knee endoprosthesis firstly has—said feature being in accordance with the prior art—a main body, a probe part, two contact pieces and at least one scale and an associated indicator. The probe part has a probe arm with a probe tip for contacting on an anterior reference point of the distal end of the patient's femur, and the probe part is displaceable relative to the main body along a measuring direction. When the displaceability of the probe part relative to the main body—with the exception of a possible rotatability, pivotability or, transverse to the measuring direction, displaceability of the probe arm relative to another element of the probe part—is in particular advantageously limited to this linear displaceability, there is in particular no possibility of pivoting or rotating the probe part relative to the main body in a plane, in which the measuring direction extends.

The contact pieces serve to contact on and to reference on respectively the medial and the lateral posterior condyle of the distal end of the patient's femur. Finally, the scale and the associated indicator serve to indicate a location of the probe part in the measuring direction relative to at least one of the contact pieces for specification of a suitable implant size.

The improvement according to the invention in such a jig is that the contact pieces, which were always firmly connected to the main body in the known prior art, can be moved relative to the main body in such a way that a distance of the probe tip to the contact pieces which is projected on the measuring direction can be set for the contact pieces in such a way that this distance is different with respect to the two contact pieces. The improvement is also that each contact piece is provided with its own scale and an associated indicator for indicating a location of the probe part in the measuring direction relative to the respective contact piece and for the resulting specification of a suitable implant size.

With the jig according to the invention the surgeon is therefore now no longer limited to determining in a global manner an anterior to posterior distance of the probe tip to the contact pieces which is valid for both condyles contacted with the contact pieces and which is projected on the measuring direction and is finally averaged, in particular in the case of an added rotation, and thus a resulting implant size. Instead, the surgeon can now individually determine a corresponding distance for each of the contact pieces, and can define therefrom an implant size which is to be selected accordingly. It may be the case that the corresponding implant size according to medial determination and the corresponding implant size according to lateral determination (in other words, the distance of the contact piece contacting on the medial posterior condyle to the probe tip, projected on the measuring direction, and the distance, projected on the measuring direction, of the contact piece contacting on the lateral posterior condyle to the probe tip) differ from one another. However, the surgeon obtains critical information here, which he can make use of in whichever way he prefers. He is thus for example able to select an implant size lying between these determined measures which he sees as suitable. On the other hand, he is also able to select on the basis of the predetermined size an external implant rotation, which can in turn result in a compensation for the size difference.

Thanks to the solution according to the invention, the surgeon is thus no longer bound by the finally only averaged and not further differentiable size specification of implant sizes which can be determined with the known jigs, but rather he is able, based on a more differentiated size determination (ultimately a size determination for a medial value and a lateral value), to make a more informed decision regarding selection of the implant size and/or positioning of the implant with respect to an external implant angle.

This procedure can be further improved with respect to surgical technique when, as early as the realization of the distal femoral cut, which typically takes place only upon resection and preparation of the distal femur end for receiving the femoral implant of the knee endoprosthesis, one of the condyles (medial or lateral) is selected with a view to the referencing, which is then also retained as a reference in the subsequent size determination. This can occur for example in the ways described in the description of the possible embodiments of the invention with reference to FIGS. 6 to 9.

A coupling can advantageously be provided in the jig according to the invention between the contact pieces, which, in the case of a relative movement of the one contact piece relative to the main body, also produces a relative movement of the other contact piece relative to the main body. Such a coupling simplifies the handling of the jig according to the invention such that, simply by the setting of a distance of one contact piece relative to the probe tip, the surgeon also repositions the second contact piece, which process does not have to occur separately and manually here. In the above-described advantageous solution, a basic position can be provided, in which the two contact pieces have the same distance to the probe tip projected on the measuring direction, wherein the coupling ensures by means of each relative movement out of the basic position between a first of the contact pieces and the main body that there is such a relative movement of the second of the contact pieces and the main body, which leads to a setting of the contact pieces in such a way that they have different distances to the probe tip projected on the measuring direction. In this way, a corresponding adaption to the different conditions actually occurring is obtained.

According to another advantageous further development of the jig according to the invention, the contact pieces can each have an extension which extends in the measuring direction and which is firmly connected to the contact piece, with the extensions being connected to one another by means of two cross pieces extending parallel to one another, and the cross pieces being connected in an articulated manner at one connection point to the respective extension, so that the two extensions and the two cross pieces form a parallelogram four point joint. In this solution, a respective cross piece is connected in an articulated manner at a first connection location, e.g. at an end, to a first of the extensions, and is likewise connected in an articulated manner at a second location, e.g. a second end, to the second of the extensions. In such a way that the two extensions are aligned parallel to one another, the second cross piece is arranged parallel to the first cross piece with a distance to the first cross piece and is likewise connected in an articulated manner to the first of the extensions by means of a first connection location, in particular a first end, with this articulated connection correspondingly having a distance to the articulated connection of the other cross piece with this extension; the second cross piece is correspondingly connected in an articulated manner to the second extension at a second connection location, in particular at its second end, with the two articulated connections of the first and of the second cross piece also being correspondingly spaced apart from one another here. A corresponding formation of the coupling between the contact pieces by means of a parallelogram four point joint formed by the extensions and the cross pieces and their respective articulated connection at the four connection points has the advantage of a simple coupling, which permits a corresponding setting of the contact pieces with different distances to the probe tip. This is particularly the case when the cross pieces, as envisaged according to another advantageous design of the invention, are connected in an articulated manner to the main body in such a way that these cross pieces can be pivoted in a coupled manner relative to the main body. This articulated connection to the main body can in particular be designed such that each of the cross pieces is connected in an articulated manner to the main body at an attachment point situated centrally between the two connection points, at which it is connected in an articulated manner in each case to one of the two extensions. This results in an even displacement of the respective end of the cross pieces connected in an articulated manner to one of the extensions in the one direction (e.g. a direction to be defined as upwards along the measuring direction), when the opposite side of the cross piece, in other words, the connection to the respective other extension, moves by a corresponding value along the measuring direction in an opposite direction (e.g. in a direction to be defined as downwards along the measuring direction).

In the coupling of the cross pieces to the main body which can be pivoted as described, at least one angle scale and an angle indicator cooperating therewith can advantageously be provided for indicating a pivot angle by which the cross pieces are pivoted relative to a starting position. This angle scale can indicate a corresponding value by which the cross pieces are pivoted relative to a starting position, said starting position being able to be, in one advantageous embodiment, the basic position mentioned in the above-described advantageous further development for example. The starting position can in particular be a longitudinal orientation of the cross pieces lying in a direction extending from lateral to medial.

Corresponding pinholes can be provided in particular in the main body, but particularly advantageously in the probe part, through which pinholes pins can then be driven into the contact plane previously created by the distal condyle cut in order to thus mark the external implant angle set by corresponding pivoting of the cross pieces for the subsequent alignment of the additional resection cuts by means of corresponding arrangement of the cutting models at the preset angle by placement using pinholes correspondingly formed in the cutting model by means of the pins previously driven into the first cutting plane as described above.

Because the parallelogram four point joint, by means of which the contact pieces are coupled in their possible relative movement relative to the main body and therefore also relative to the probe tip, produces both a corresponding shift of the distance projected on the measuring direction between the probe tip and the respective contact piece (medial or lateral) and also a setting of the external implant angle, the surgeon can by this means determine the relationship between the different indicated implant sizes and the specified external implant angle and, for example, select the external implant angle in such a way that the implant sizes indicated for medial and lateral are aligned as much as possible in order to thus be able to optimally undertake a size selection of the femoral implant. Alternatively, the surgeon can however also specify an external implant angle which he prefers and then read the medial and lateral implant size from the respective scale and, in the event of different results, select an implant sizes suited to his surgical technique on the basis of his own experience.

To facilitate handling of the jig according to the invention by the surgeon, a handle can advantageously be provided, which handle can in particular be connected to the main body.

In addition, a locking means, as envisaged according to another advantageous further development of the invention, for locking parts of the jig which can move relative to one another, can assist the surgeon with fixing the once selected position of the jig with regards to the set distances of the two contact pieces projected on the measuring direction and— should it occur—with regards to a tilting of the alignment position from the lateral to the medial, in order to maintain a value which has been once set, and to be able to replicate this value if appropriate even after removal of the jig from the contact on the cutting plane of the distal condyle cut. Such a locking means can for example be a set screw.

In addition, the jig according to the invention can advantageously be disassemblable so as to allow said jig to be easily cleaned and disinfected after use. The jig is particularly advantageously able to be disassembled without the use of tools because individual parts are connected to one another for example by means of force-fit type snap connections or by means of form-fit type connections which are detachable from one another in a specific position.

Individual movement ranges of the parts of the jig which can be moved relative to one another can be delimited in particular by means of stops formed between these parts. It is thus possible to determine movement ranges which are typically considered to be plausible, which cannot be exceeded. This assists the surgeon with the use of the jig according to the invention, as he does not need to worry for example about exceeding the plausible ranges of a setting with this jig.

Figure 2:
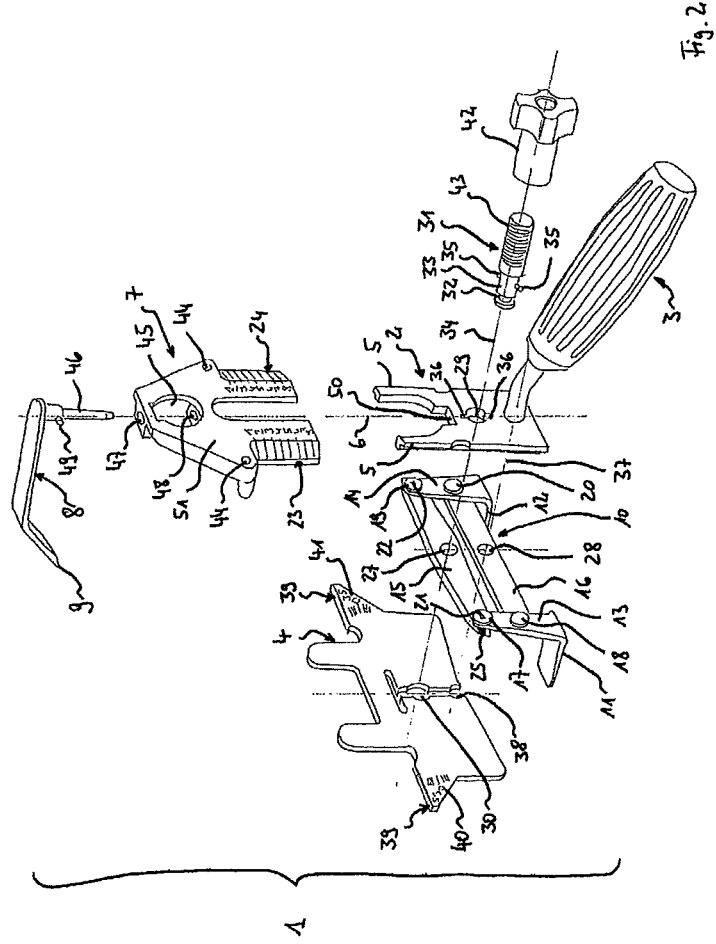
FIG. 2 shows, in an exploded view, an exemplary embodiment of a jig according to the invention with contact pieces which can be individually set with respect to their distance to the probe tip projected on the measuring direction.

FIG. 2 depicts, in a sketch-form exploded view, an exemplary embodiment of a jig according to the invention for determining a patient-adapted implant size of the femoral implant of a knee endoprosthesis. This jig, which is generally identified with the reference numeral 1, serves in the depicted exemplary embodiment not only for the size determination of the implant, but also for determining or for specifying the alignment according to the external implant angle.

The jig 1 firstly has a holding and guiding part 2, on which a handle 3 is integrally formed. During usage a counter piece 4 is connected to the holding and guiding part 2 in a fixed manner and non-displaceable relative to one another. The holding and guiding part 2 and the counter piece 4 thus form a main body of the jig 1.

A probe part 7 is placed on laterally projecting guide rails 5 which are formed on the holding and guiding part 2 in such a way that it is displaceable in a measuring direction along the line 6. A probe arm 8 is a component of the probe part 7 and is detachably arranged on a slide element 51 of said probe part and is pivotable relative thereto about the axis 6, which probe arm has a probe tip 9 on an end extending in a bent manner on the front edge thereof. This probe tip 9 does not have a tip which is pointed, for example, in the depicted exemplary embodiment, but instead forms an edge-type or linear extension, which is nevertheless also described as a "probe tip" here because it contacts on an anterior reference point.

A contact part 10 can also be seen. This contains two contact pieces 11, 12, which are formed approximately plate-shaped here. The contact pieces 11, 12 are connected in an integral manner to extensions 13, 14 extending approximately perpendicular to said contact pieces. The extensions 13, 14 are oriented parallel to one another and extend in the assembled state of the jig 1 parallel to the measuring direction indicated by the axis 6.

Two cross pieces 15, 16, which are in turn arranged parallel to one another in their longitudinal extension, are arranged between the extensions 13, 14, which cross pieces are each connected in an articulated manner to the extensions 13, 14 at connection points 17, 18, 19, 20. In this design, the extensions 13, 14 together with the cross pieces 15, 16 form a parallelogram four point joint.

Indicator markers 21, 22 are introduced in the region of the connection points 17, 19, which indicator markers lie, in the assembled state of the jig 1, opposite a left and a right scale 23, 24 on the probe part 7 and serve for corresponding indication on the respective scale 23 or 24. Another indicator marker 25 can be seen on a lateral projection of the cross piece 15 in the region of the extension 13, with another such indicator marker 26 being introduced on the opposite side on another lateral projection of the cross piece 15, as can be seen in FIG. 4.

Finally, it can be seen here that openings 27 and 28 are introduced into the cross pieces 15, 16 in each case centrally between the connection points 17, 19 and 18, 20 lying opposite one another. In the assembled state of the jig 1, the opening 27 lies in alignment with another opening 29 in the holding and guiding part 2 and a clamp opening 30 in the counter piece 4. For the purpose of assembly, a retaining and threaded bolt 31 is introduced through the opening 29 and the opening 27 and into the clamp opening 30. This retaining and threaded bolt is fixed there with an undercut 32 lying on its first end. The opening 27 rests on a smooth-walled section 33 of the retaining and threaded bolt, so that this opening can rotate about the axis which is defined by the retaining and threaded bolt 31 and which is indicated with the reference numeral 34. In a first rotational position of the retaining and threaded bolt 31, lateral locking pins 35 pass through corresponding recesses 36 at the edge of the opening 29 and lock the holding and guiding part 2 when the retaining and threaded bolt 31 is rotated out of the alignment of the locking pins 35 with the recesses 36. On the side opposite the connection of the handle 3 to the holding and guiding part 2 another clamping pin, which is not visible in this depiction, is integrally formed, which extends along another axis 37 and, in the assembled state, projects through the opening 28 in the cross piece 16 and which, with an undercut comparable to the undercut 32 on the retaining and threaded bolt 31, sits wedged in another clamp opening 38 in the counter piece 4.

Figure 4:
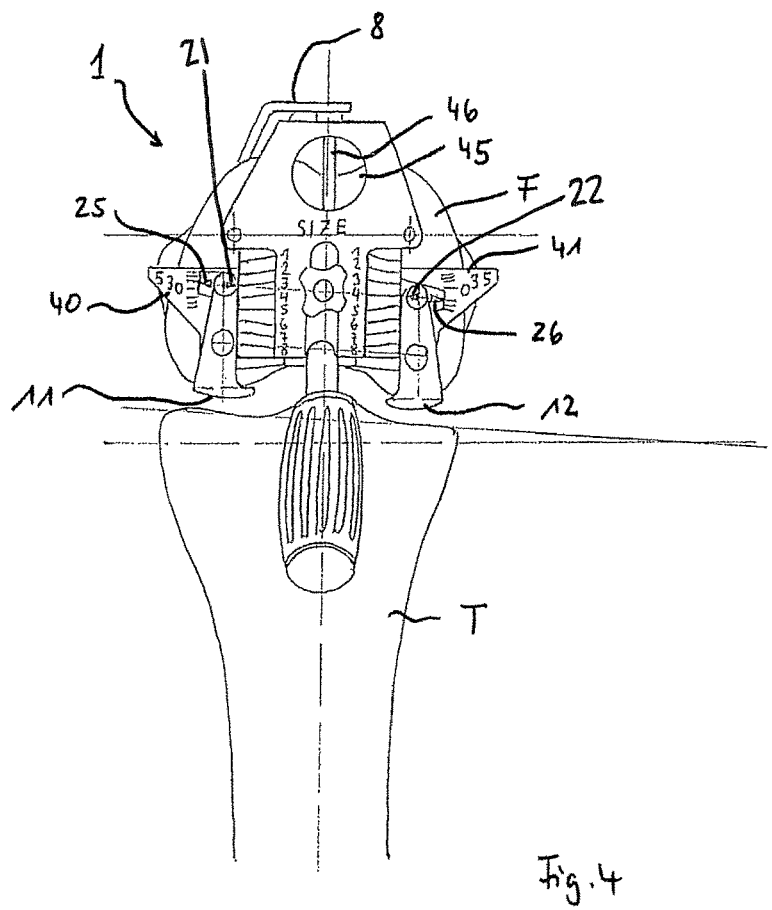
FIG. 4 shows a front view of the jig according to the exemplary embodiment according to FIG. 2 placed on the distal end of the femur with the knee in a flexed position and of the distal end of the resection cut already applied there, in other words, of the cutting plane.

The counter piece 4 has an angle scale 40, 41 on each of two indicator-type outwards facing side flanges 39, which angle scales cooperate with the indicator markers 25 and 26, as can be seen in particular in FIG. 4, in order to indicate the setting of an external implant angle. The indicator-type tapered shape of the side flanges 39 is intended to assist the surgeon with an intuitive alignment of the counter piece 4 connected to the holding and guiding part 2, in particular for the alignment of a theoretical connecting line between the medial and the lateral epicondyle.

A nut 42 with an internal thread can be screwed to an external thread 43 formed on the retaining and threaded bolt 31 in order to apply, in particular in the case of firm tightening of the nut 42, a pressure onto the front side of the holding and guiding part 2 facing the handle 3 or to apply a tractive force to the counter piece 4 and thus clamp the parts, which can be moved relative to one another in the manner described in greater detail below, in an assumed relative position relative to one another (this does not apply to the probe arm 8 of the probe part 7 which is pivotable relative to the slide element 51). Finally, two pinholes 44 and one sighting hole 45 can be seen on the probe part 7. The pinholes 44 serve for the precise positioning of marking pins once the jig 1 has been set, the sighting hole 45 helps the surgeon to locate looking through said sighting hole a pivot pin 46 of the probe arm 8 which extends centrally through the sighting hole 45 and thus to align the jig according to the invention or check its alignment by targeting the anterior intercondylar fossa.

In order to assemble the jig 1 according to the invention, the slide element 51 of the probe part 7 is placed on the guide rails on the holding and guiding part 2, the retaining and threaded bolt 31 is passed through the opening 29 and the opening 27, and the pin which cannot be seen in great detail in FIG. 2 and which is formed on the side opposite the connection of the handle 3 to the holding and guiding part 2 is also passed through the opening 28. The counter piece 4 is then clamped on the ends of the retaining and threaded bolt 31 and of the connecting pin 38 (not depicted here), and finally the nut 42 is screwed onto the external thread 43 of the retaining and threaded bolt 31. The probe arm 8 is introduced by means of its pivot pin 46 into pivot bearing openings 47, 48 provided for this purpose in the slide element 51 and it is secured by means of rotation of a locking pin 49 from an installation position into a use position. The lower end of the pivot pin 46, which contacts a stop surface 50, now prevents the probe part 7 from being further displaced in the measuring direction (axis 6) in FIG. 2 in a downwards direction as far as a disassembly position. The jig 1 is thus secured in this assembled position.

During usage, it is now possible to move not only the probe part 7 in a position which is displaceable along the axis 6, in other words, the measuring direction, relative to the main body formed by the holding and guiding part 2 and the counter piece 4, the contact pieces 11, 12 can also be moved relative to this main body and this occurs in such a way that different height settings or distance values to the probe tip 9 projected on the measuring direction (axis 6) are obtained for the contact pieces 11, 12. This setting occurs by means of a movement of the four point parallelogram joint, which pivots by means of a pivoting of the cross pieces 15 and 16 about the retaining and threaded bolts 31 and (not depicted) connecting pin guided through the openings 27 and 28 forming the pivot bearing about the axes 34 and 37. This pivot movement at the same time results in a setting of the external implant angle from a normal position perfectly aligned medially to laterally along the epicondyles, which setting is shifted by an angle. During use, this pivot angle can then be read in a cooperation of the indicator markers 25, 26 with the angle scales 40, 41 and the respective implant size with respect to the contact piece 11 or the contact piece 12 can be read on the associated scale 23 or 24 by means of indication of the indicator markers 21 or 22.

Figure 3:
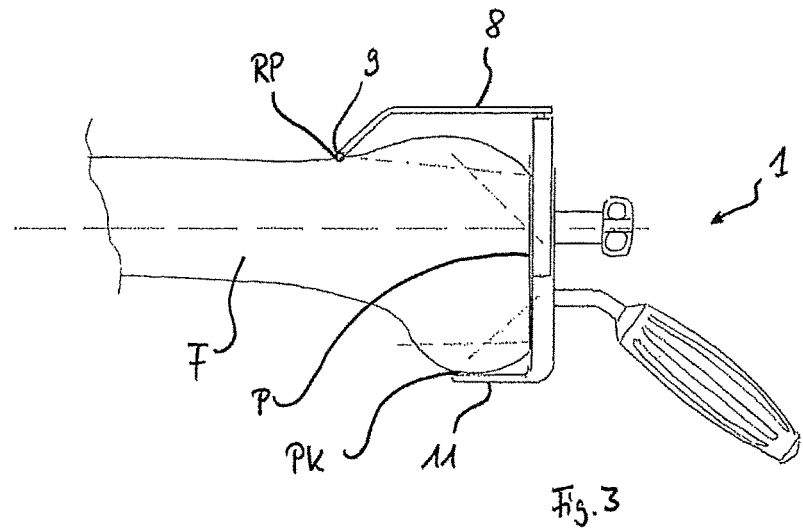
FIG. 3 shows a side view of a jig according to the invention according to FIG. 2 placed on the distal femur end after realization of the distal resection cut.

FIG. 3 now depicts the jig 1 according to the invention schematically and in a side view, said jig being set against a plane surface P, which is produced by the already realized distal condyle cut, and contacting, by means of the probe arm 8 and the probe tip 9 arranged thereon, a reference point RP on the anterior of the femur F. It is also possible to see here how the contact piece 11 contacts a posterior condyle PK and the jig references this posterior condyle.

FIG. 4 shows the situation from FIG. 3 once again in a view of the distal end of the femur F, with this figure also depicting the dorsal section of the tibia T in order to make it clear that the connection of the jig 1 according to the invention takes place in flection. It can also be seen here how, by means of the sighting hole 45, the pivot pin 46 of the probe arm 8 points to the fossa of the anterior condyle extensions and thus constitutes an alignment aid for the surgeon.

Figure 5:
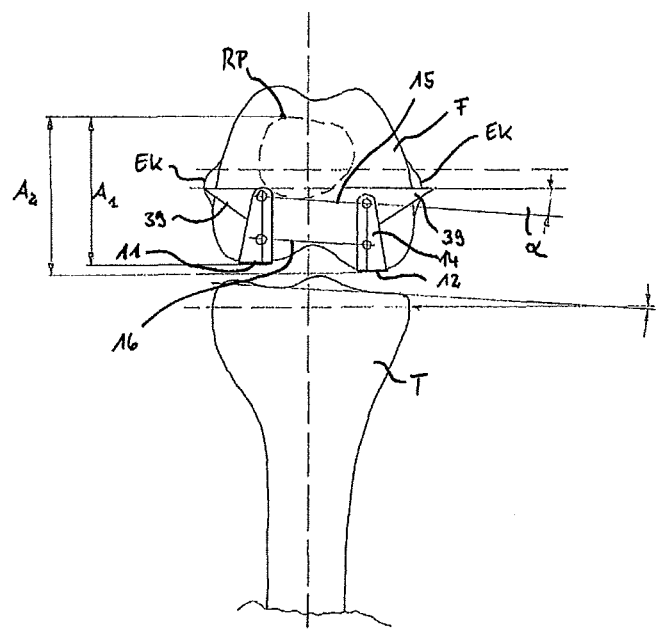
FIG. 5 shows a simplified schematic depiction of only the coupling of the two contact pieces by means of the parallelogram four point joint and the thus obtained different distance setting to the reference point contacted by means of the probe tip of the probe, in other words, to the location of the probe tip.

FIG. 5 is a schematic view of the distal end of the femur with an additionally depicted proximal end of the tibia, wherein, on the contact surface already prepared on the distal condyle cut, the jig 1 contacting thereon is depicted only by means of and reduced down to the elements essential to the explanation with reference to this figure and the interrelationships shown therein. Only the side flanges 39 of the counter piece 4 are shown, which counter piece is part of the main body, as well as—depicted in a highly schematic manner—the parallelogram four point joint consisting of the extensions 13 and 14 and the cross pieces 15, 16, which are only schematically depicted as lines here. There is likewise an indication of the contact pieces 11 and 12, which are arranged medially and laterally on the posterior condyles.

In this depiction, it is possible to see on the one hand how the indicator-type tapered side flanges 39 assist the surgeon for a further orientation of the positioning of the jig 1 in that these are namely aligned with the connecting line of the two epicondyles EK, the medial epicondyle and the lateral epicondyle. It can also be seen that, by means of a corresponding relative displacement of the parallelogram four point joint relative to the main body, which the side flanges 39 constitute a component of, an angular offset $\alpha$ is formed, which is also manifested in a different height or a different distance of the attachment pieces 11 and 12 to the reference point RP, which the probe tip 9 contacts (cf. FIG. 3). The attachment piece 11, which can be for example laterally arranged in the example depicted here, has a distance $A_1$ to the reference point along the measuring line, which distance is noticeably smaller than the distance $A2$ which the attachment piece 12, arranged laterally for example in this example, presents with respect to the reference point RP projected on the measuring direction. Thanks to the particular design of the parallelogram four point joint, to which the contact pieces 11, 12 are connected by means of the extensions 13, 14 and the cross pieces 15, 16 and which is linked in the rotatable manner described above to the main body formed by the holding and guiding part 2 and the counter piece 4, a height distance (the distance to the reference point RP projected on the measuring direction) is determined which differs according to the respective contact surface (medial or lateral) and thus a suitable value for the size determination of the implant is determined for both of the sides. By means of corresponding repositioning of the angle setting, the surgeon is here able to select the parameters such that the sizes specifications are similar to one another, so that he can select an optimal and suitable implant size and a corresponding femoral implant and is then immediately able to determine and fix the appropriate position for this femoral implant relative to the external implant angle.

In order to generally facilitate the procedure which is permitted by the use of the jig according to the invention, namely, the targeted referencing during the determination of the femoral implant size on one of the two condyles (lateral or medial) or to further harmonize the entire surgical technique with this basic concept of specific referencing on either the lateral or the medial condyle, corresponding measures of a selected referencing can be undertaken as early as the creation of the distal condyle cut or in conjunction with the realization of this cut.

Figure 6:
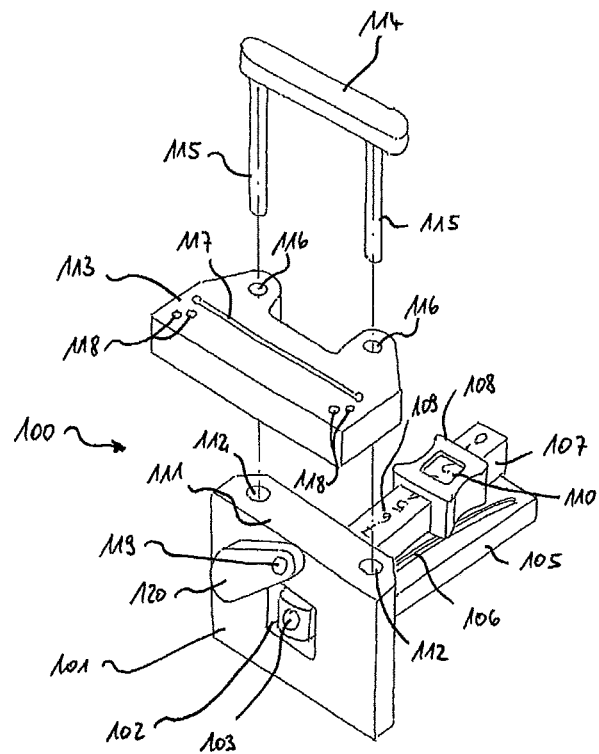
FIG. 6 shows an alignment instrument for the distal femur cut which can be used for an advantageous targeted referencing on a selected condyle (medial or lateral) for use as part of the full set of surgical instruments together with a jig according to the invention in a three-dimensional depiction which is partially shown in an exploded form.

A first option for doing this is to use a modified alignment instrument for the alignment of a cutting guide for the distal condyle cut as depicted in FIG. 6.

The alignment instrument depicted in FIG. 6 is generally assigned the reference numeral 100 and is depicted in a three-dimensional view in this figure. It has a contact plate 101 for contacting with the distal condyle of a femur. The contact plate 101 has a central opening 102 through which a rod support 103 formed as an elongated opening can be accessed. This rod support 103 serves to support an intramedullary rod 104 which is typically itself used in the orientation and alignment of the alignment instrument 100 and which is introduced into an axial bore in the distal femur (cf. FIG. 7a and FIG. 7b). The alignment instrument 100 depicted in FIG. 6 additionally has an angle adjustment means for setting an angular offset relative to a perpendicular direction to the axial direction of the intramedullary rod 104 for the cutting plane to be set. This angle adjustment is released by means of an extension 105 fixed on the contact plate 101, which extension has curved guide grooves 106 on its surface which faces upwards in the depiction in FIG. 6 (only one of the guide grooves 106 can be seen here). The element, in which the rod support 103 is introduced, a guide strip 107, supports a slider 108 which can be moved longitudinally on this guide strip 107. On its side facing the top side with the guide grooves 106 of the extension 105, the slider has a cone-shaped projection, by means of which said slider engages in one of the guide grooves 106 and is thus guided by the guide groove 106. By means of a longitudinal displacement of the slider 108 along the guide strip 107, a guided relative pivoting between the extension 105 and the guide strip 107 is thus obtained, so that the guide strip 107 can, in an articulated mounting (not depicted in great detail here) in the opening 102, pivot in an angle setting relative to the contact plate 101. On the top side depicted at the top in FIG. 6, the guide strip 107 has an angle scale 109. This scale can be read through a reading hole 110 in the slider 108, and the set pivot angle can thus be determined.

Two fastening openings 112 are introduced transverse to a top edge 111 of the contact plate 101. These fastening openings serve to fix a cutting guide block 113 to the alignment instrument 100. By means of a double pin lock 114, which has two fastening pins 115 extending in parallel, the cutting guide block 113 is fixed on the top edge 111, by introducing the fastening pins 115 of the double pin lock 114 through corresponding openings 116 in the cutting guide block 113 and into the fastening openings 112. In this manner the cutting guide block 113 is then fixed on the top edge 111 and a guide slot 117, provided as a cutting guide for the saw blade of a cutting instrument, is thus also defined in a corresponding alignment and orientation to the distal femur. By means of fastening pins being passed through pinholes 118 provided on the cutting guide block 113 and being driven into the bone material of the distal femur end, the cutting guide block 113 can also be fixed directly on the bone, so that the alignment instrument 100 and also the double pin lock 114 can be removed in a conventional manner before the distal resection cut is undertaken with guidance by means of the guide slot 117.

In terms of the elements and functions described up until now, the alignment instrument 100 depicted in FIG. 6 and described above conforms to conventional and known alignment instruments. The aspect which is novel and which is provided for the adaptation, as described above, to a novel surgical technique with deliberate referencing to a selected one of the condyles is a contact piece 120 which is pivotably fixed on the contact plate at an articulation point 119 and which has significant thickness and is thus virtually block-shaped.

This contact piece 120, which can more generally be described as a contact element or referencing element and which can take very different forms which differ from the embodiment depicted in FIG. 6, can be pivoted between the position as depicted in FIG. 6 and at least another position, in which the contact piece 120 is displaced towards another side of the contact plate 101, in order to thus, with selected referencing of one of the two condyles, namely the medial condyle or the lateral condyle, be brought into contact on this selected condyle in a targeted manner.

This is depicted in FIGS. 7a and b, where the alignment instrument 100 is depicted in use in two examples on a femur F of the left leg. In FIG. 7a, by means of corresponding orientation of the pivot position of the contact piece 120, said contact piece is set in such a way that it contacts the lateral condyle, and is thus referenced in the alignment with this lateral condyle. In the depiction in FIG. 7b, the contact piece 120 has been pivoted into its second position, in which it now contacts the medial condyle, and the alignment is accordingly undertaken referencing said condyle. As can be clearly seen, the alignment instrument 100 with its contact plate 101 does not contact, in the respective alignment of the contact piece 120, the condyle not contacted by the alignment piece 120, so that no referencing takes place at this location, and the referencing occurs exclusively by means of the condyle which is referenced by means of corresponding alignment of the contact piece 120. It can also be clearly seen that, due to the different referencing in FIGS. 7a and 7b, different distances of the alignment instrument 100 to the femur F are obtained, which is associated with a different position of the cutting plane of the distal femur cut, which is set with this alignment, in the distal to dorsal direction.

Another means or another option for including a referencing to one of the condyles here as early as the planning of the distal resection cut is depicted based on the additional FIGS. 8 and 9. FIG. 8 depicts an alternative alignment instrument 130 as is used in order to align and to plan the cutting line for the distal resection cut DS on the distal femur F. In terms of its basic construction, this alignment instrument 130 resembles the alignment instrument 100 described previously with reference to FIGS. 6 and 7. Accordingly, parts with the same construction are therefore also depicted with the same reference numerals in FIG. 8 in the case of the alignment instrument 131. Here too, a guide strip 107 is pushed onto an intramedullary rod 104. Arranged relative to this guide strip 107 about a pivot axis S (extending perpendicular to the drawing plane in the figure) is a body formed by an attachment 101 with an extension 105, which body can, by means of pivoting about the pivot axis S, be set in its angle setting relative to the alignment of the intramedullary rod 104. For this purpose, the slider 108 is used in the manner described above with reference to the example according to FIG. 6/7, which slider can be linearly moved over the guide strip 107 and which has an angle scale 109, by means of which the set angle can be easily read through the reading hole 110 in the slider 108. The distinctive aspect of this alignment instrument 130 is the manner of referencing. This takes place by means of a contacting tip 131 guided in extension of the contact plate 101 (which then thus no longer actually contacts on the condyles) along the axis along which the intramedullary rod 104 extends. This contacting tip is formed such that it contacts, by means of its front end facing away from the contact plate 101, the trochlea TR of the distal end of the femur F. In this type of referencing on the trochlea TR it is understood that this region (the region of the trochlea TR) is to not remain unworked in the resection. Specifically, the there-located region of the patella sliding groove should not remain unworked in order to in particular prevent a distalization of the implant location or of the patella sliding groove. With this requirement, the patella sliding groove is thus used as distal reference in a de facto manner as depicted in FIG. 8.

If the resection is, after such referencing and definition of the resection plane, now carried out with the help of a cutting guide block 113 fixed on the contact plate 101 as in the case of the alignment instrument 100 (depicted in FIG. 6), wherein this leads along the resection line of the distal cut identified with DS in FIG. 8, which, as depicted, then lies, on the basis of the referencing on the trochlea, in such a way that a continuous surface is formed between the medial and lateral condyle by means of this cut. Sections are accordingly obtained, which come from the existing natural (remaining) condyles. The thus occurring sections are now measured by means of a simple jig 140 depicted in FIG. 9 in order to determine their thickness, with this thickness being related to the implant thickness and an implant size or an implant size parameter thus being able to be determined. For this purpose, the jig 140 has two shanks 142, 143 lying opposite one another, which surround a wedge-shaped opening 141. The section AS can be inserted into this wedge-shaped opening until it is clamped therein. The position of the stop of the section AS can then be read on a scale 144 introduced onto the shank 143 depicted at the bottom in FIG. 9, in this example this position lies between the scale values 7 and 8. These scale values can be already selected and measured such that they represent and reflect corresponding implant sizes, so that a first referencing on the medial or lateral side can thus take place in that, by means of measurement of the two sections AS of the medial or the lateral condyle, there is definition and determination of which of the two condyles should determine the implant size thus ascertained.

The above-described additional instruments and procedures depicted by means of FIGS. 6 to 9, which are presented here as additional options for proceeding in the overall surgical process, in which process the jig according to the invention and as described above is also used, can individually contain separate inventions and can in particular also have applications and uses without connection to the jig according to the invention described and claimed here. In this respect they are to be considered to be separate technical developments.

The above description of an exemplary embodiment of the jig according to the invention has again illustrated the advantages thereof and the method of operation and the type of application of this jig. The description of the exemplary embodiment does not of course limit the invention to this specific exemplary embodiment. Instead, the general scope and significance of the invention is defined by the following claims.

LIST OF REFERENCE NUMERALS 1 jig
2 holding and guiding part
3 handle
4 counter piece
5 guide rail
6 axis
7 probe part
8 probe arm
9 probe tip
10 contact part
11 contact piece
12 contact piece
13 extension
14 extension
15 cross piece
16 cross piece
17 connection point
18 connection point
19 connection point
20 connection point
21 indicator marker
22 indicator marker
23 scale
24 scale
25 indicator marker
26 indicator marker
27 opening
28 opening
29 opening
30 clamp opening
31 retaining and threaded bolt
32 undercut
33 smooth-walled section
34 axis
35 locking pin
36 recess
37 axis
38 clamp opening
39 side flange
40 angle scale
41 angle scale
42 nut
43 external thread
44 pinhole
45 sighting hole
46 pivot pin
47 pivot bearing opening
48 pivot bearing opening
49 locking pin
50 stop surface
51 slide element
100 alignment instrument
101 contact plate
102 opening
103 rod support
104 intramedullary rod
105 extension
106 guide groove
107 guide strip
108 slider
109 angle scale
110 reading hole
111 top edge
112 fastening opening
113 cutting guide block
114 double pin lock
115 fastening pin
116 opening
117 guide slot
118 pinhole
119 articulation point
120 contact piece
130 alignment instrument
131 contacting tip
140 jig
141 wedge-shaped opening
142 shank
143 shank
144 scale
α angular offset
A distance
$A_1$ distance
A2 distance
AP alignment point
AS section
DS distal resection cut
DZ rotation center
EK epicondyle F femur
L line
OL1 orientation line
OL2 orientation line
P plane surface
PK posterior condyle
RP reference point
S pivot axis
T tibia
TR trochlea

The invention claimed is:

1. A jig for determining a patient-adapted implant size of a femoral implant of a knee endoprosthesis, wherein the jig comprises:
a main body;
a probe part displaceable relative to the main body along a measuring direction, wherein the probe part includes:
a probe arm with a probe tip adapted to contact on an anterior reference point (RP) of a distal end of a patient's femur;
two contact pieces adapted to contact on and reference on respectively a medial posterior and a lateral posterior condyle of the distal end of the patient's femur; and
at least one scale and an associated indicator adapted to indicate a location of the probe part in the measuring direction relative to at least one of the contact pieces for a specification of a suitable implant size; wherein the contact pieces are movable relative to the main body in such a way that a distance of the probe tip to the contact pieces which is projected on the measuring direction is settable for the contact pieces in such a way that the distance is different with respect to the two contact pieces, and in that each contact piece is provided with its own scale and an associated indicator for indicating the location of the probe part in the measuring direction relative to the respective contact piece and for the resulting specification of the suitable implant size.

2. The jig according to claim 1, further comprising a coupling existing between the two contact pieces, which, in the case of a relative movement of a first of the two contact pieces relative to the main body, also produces a relative movement of a second of the two contact pieces relative to the main body.

3. The jig according to claim 2, further comprising a basic position in which each of the two contact pieces have a same distance to the probe tip projected in the measuring direction; and wherein the coupling ensures that each of the two contact pieces is separately movable relative to the main body and thereby out of the basic position and the movement of one or both of the two contact pieces relative to the main body leads to a setting of the two contact pieces in such a way that the two contact pieces have different distances to the probe tip projected in the measuring direction.

4. The jig according to claim 3, wherein the contact pieces each have an extension which extends in the measuring direction and which is firmly connected to the contact piece, with the extensions being connected to one another by means of two cross pieces extending parallel to one another, the cross pieces being connected in an articulated manner at one connection point to the respective extension, so that the two extensions and the two cross pieces form a parallelogram four point joint.

5. The jig according to claim 4, wherein the cross pieces are connected in an articulated manner to the main body in such a way that the cross pieces are pivotable in a coupled manner relative to the main body.

6. The jig according to claim 5, wherein each of the cross pieces is connected in an articulated manner to the main body at an attachment point situated centrally between the two connection points at which each cross piece is connected in an articulated manner to one of the two extensions.

7. The jig according to claim 5, further comprising at least one angle scale and an angle indicator which cooperates with said angle scale for indicating a pivot angle about which the cross pieces are pivoted relative to a starting position.

8. The jig according to claim 7, wherein the starting position is the basic position.

9. The jig according to claim 1, further comprising:
a handle which is connected to the main body.

10. The jig according to claim 1, further comprising a locking mechanism that locks parts of the jig that are movable relative to each other.

* * * * *